US009863869B2

(12) United States Patent
Yasuno et al.

(10) Patent No.: US 9,863,869 B2
(45) Date of Patent: Jan. 9, 2018

(54) POLARIZATION-SENSITIVE OPTICAL IMAGE MEASURING SYSTEM AND PROGRAM INSTALLED IN SAID SYSTEM

(71) Applicant: UNIVERSITY OF TSUKUBA, Tsukuba-shi, Ibaraki (JP)

(72) Inventors: Yoshiaki Yasuno, Tsukuba (JP); Deepa Kamath Kasaragod, Tsukuba (JP)

(73) Assignee: UNIVERSITY OF TSUKUBA, Tsukuba-Shi (JP)

( * ) Notice: Subject to any disclaimer, the term of this patent is extended or adjusted under 35 U.S.C. 154(b) by 0 days.

(21) Appl. No.: 15/315,275

(22) PCT Filed: Jun. 3, 2015

(86) PCT No.: PCT/JP2015/066002
§ 371 (c)(1),
(2) Date: Nov. 30, 2016

(87) PCT Pub. No.: WO2015/186726
PCT Pub. Date: Dec. 10, 2015

(65) Prior Publication Data
US 2017/0199116 A1  Jul. 13, 2017

(30) Foreign Application Priority Data
Jun. 6, 2014 (JP) .................................. 2014-118159

(51) Int. Cl.
*G01B 9/02* (2006.01)
*G01N 21/21* (2006.01)

(52) U.S. Cl.
CPC ......... *G01N 21/21* (2013.01); *G01B 9/02044* (2013.01); *G01B 9/02091* (2013.01);
(Continued)

(58) Field of Classification Search
CPC ............ G01B 9/02091; G01B 9/02044; G01B 9/02083
See application file for complete search history.

(56) References Cited

U.S. PATENT DOCUMENTS

| 7,742,173 B2 * | 6/2010 | Yun ..................... G01N 21/4795 356/479 |
| 9,330,092 B2 * | 5/2016 | Vakoc ...................... G06F 17/30 |
| 2016/0313112 A1 * | 10/2016 | Yamanari ............... A61B 3/102 |

FOREIGN PATENT DOCUMENTS

| JP | H11325849 A | 11/1999 |
| JP | 2002310897 A | 10/2002 |

(Continued)

OTHER PUBLICATIONS

International Search Report (ISR) dated Sep. 8, 2015, issued for International Application No. PCT/JP2015/066002.

*Primary Examiner* — Jonathan Hansen
(74) *Attorney, Agent, or Firm* — Law Office of Katsuhiro Arai

(57) ABSTRACT

In polarization-sensitive optical image measurement, noise-containing OCT signals obtained by polarization OCT are processed using a birefringence calculation algorithm, to obtain measured birefringence, after which noise is statistically adjusted to simulate a measured birefringence distribution and determine the noise characteristics of the measured birefringence values, and then Monte Carlo calculations are repeated by assuming different values for the noise level and the true birefringence value, respectively, to form three-dimensional histogram of combinations of true birefringence values, SN ratios, and measured birefringence values, after which specified measured birefringence values and SN ratios are assumed from the three-dimensional histogram information to obtain a true birefringence probability density distribution, and true birefringence values are (Continued)

estimated from the true birefringence probability density distribution.

18 Claims, 5 Drawing Sheets

(52) U.S. Cl.
CPC .. *G01B 2290/70* (2013.01); *G01N 2201/0683* (2013.01); *G01N 2201/12* (2013.01)

(56) References Cited

FOREIGN PATENT DOCUMENTS

| | | |
|---|---|---|
| JP | 2004028970 A | 1/2004 |
| JP | 2007298461 A | 11/2007 |
| JP | 2009031229 A | 2/2009 |
| JP | 4344829 B2 | 7/2009 |
| JP | 2013019773 A | 1/2013 |

* cited by examiner

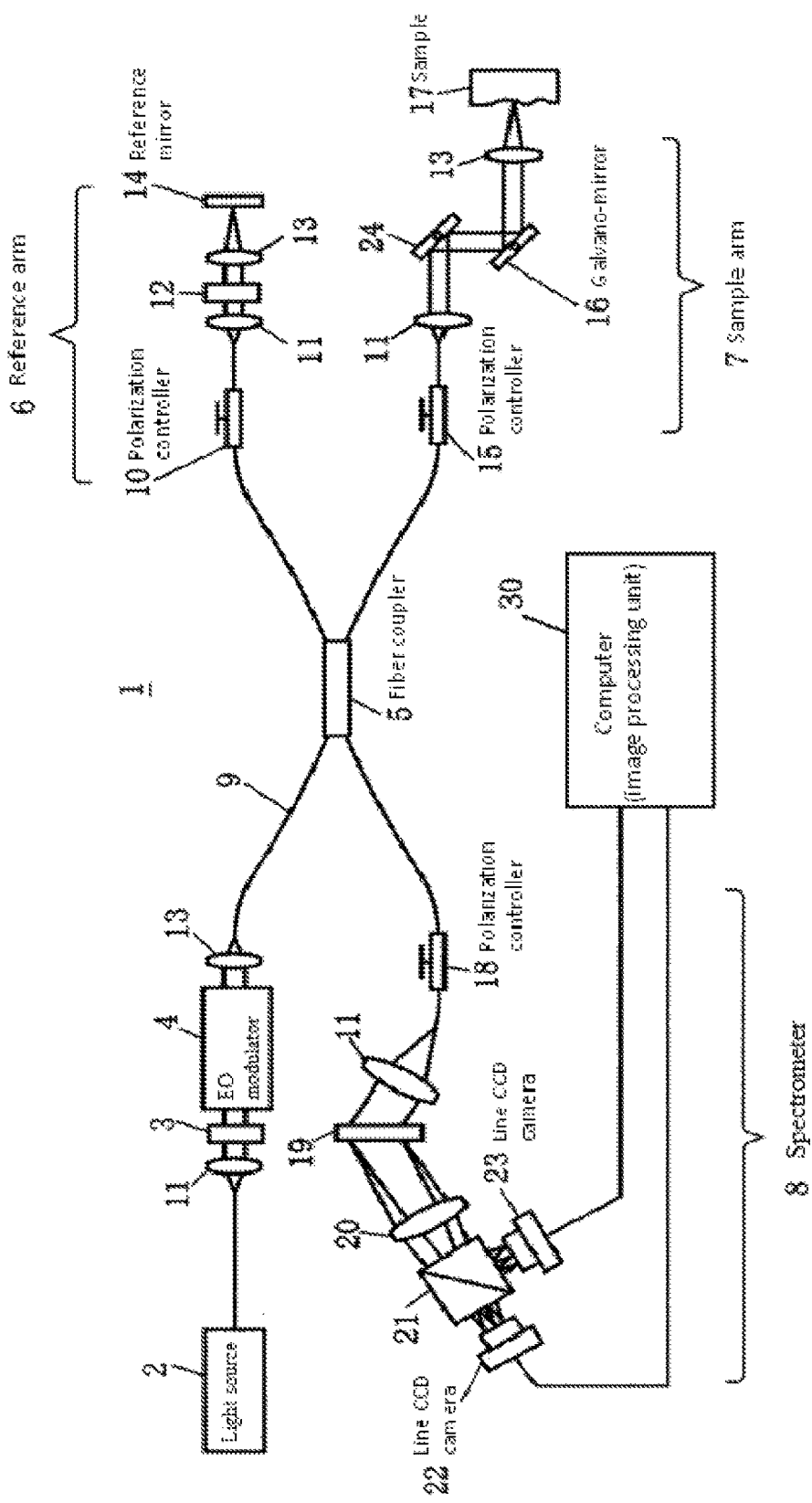
[FIG. 1]

[FIG. 2]
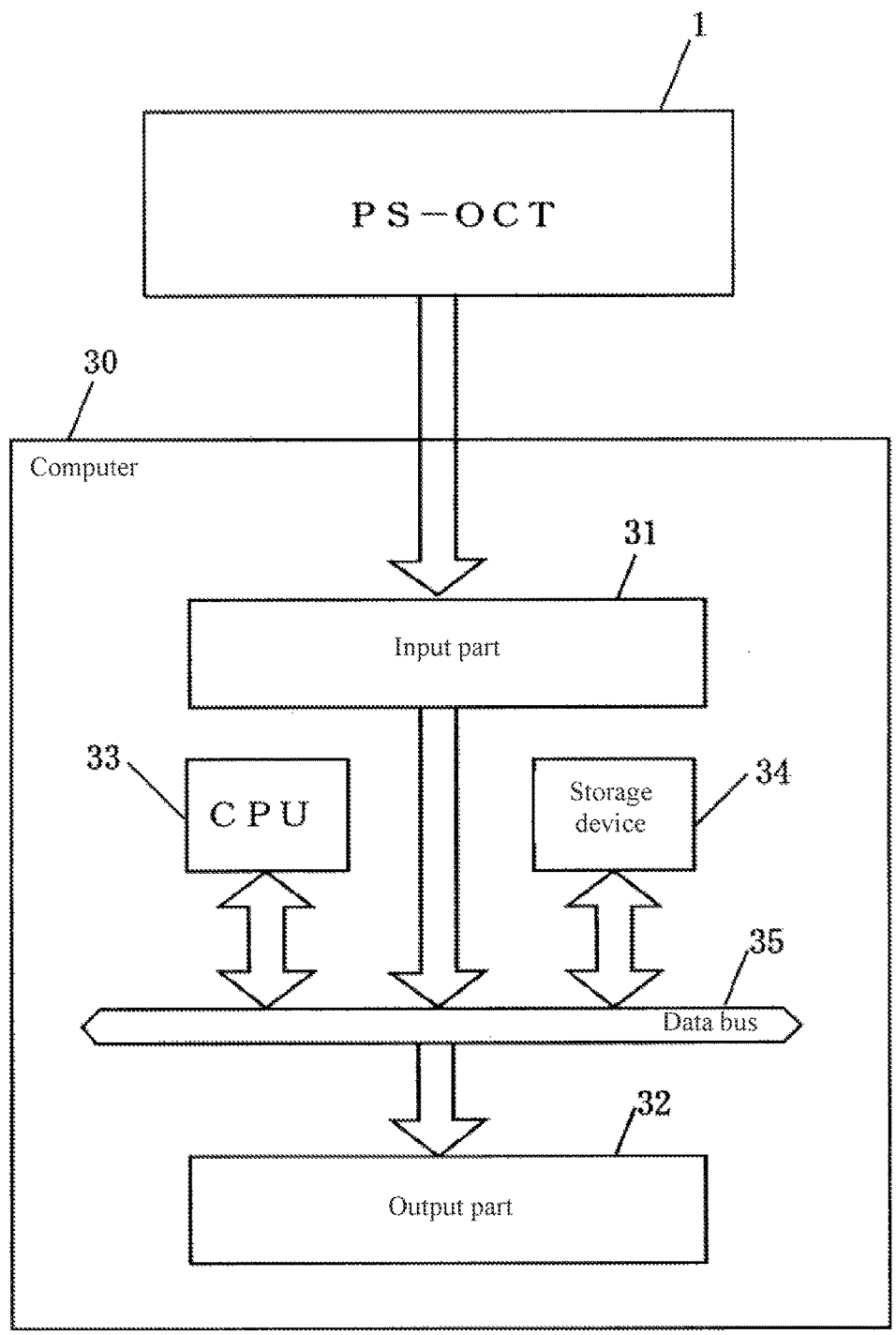

[FIG. 3]
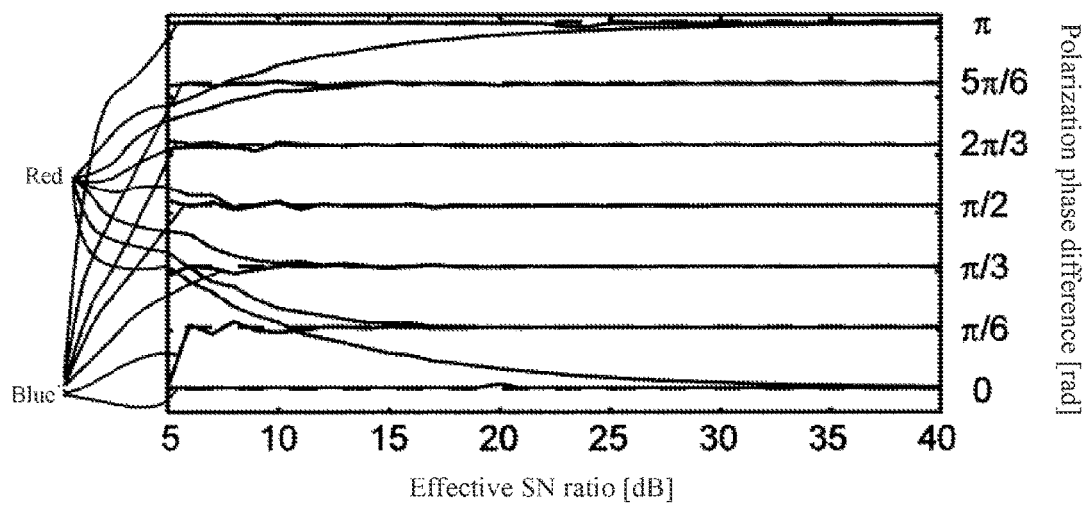

[FIG. 4]
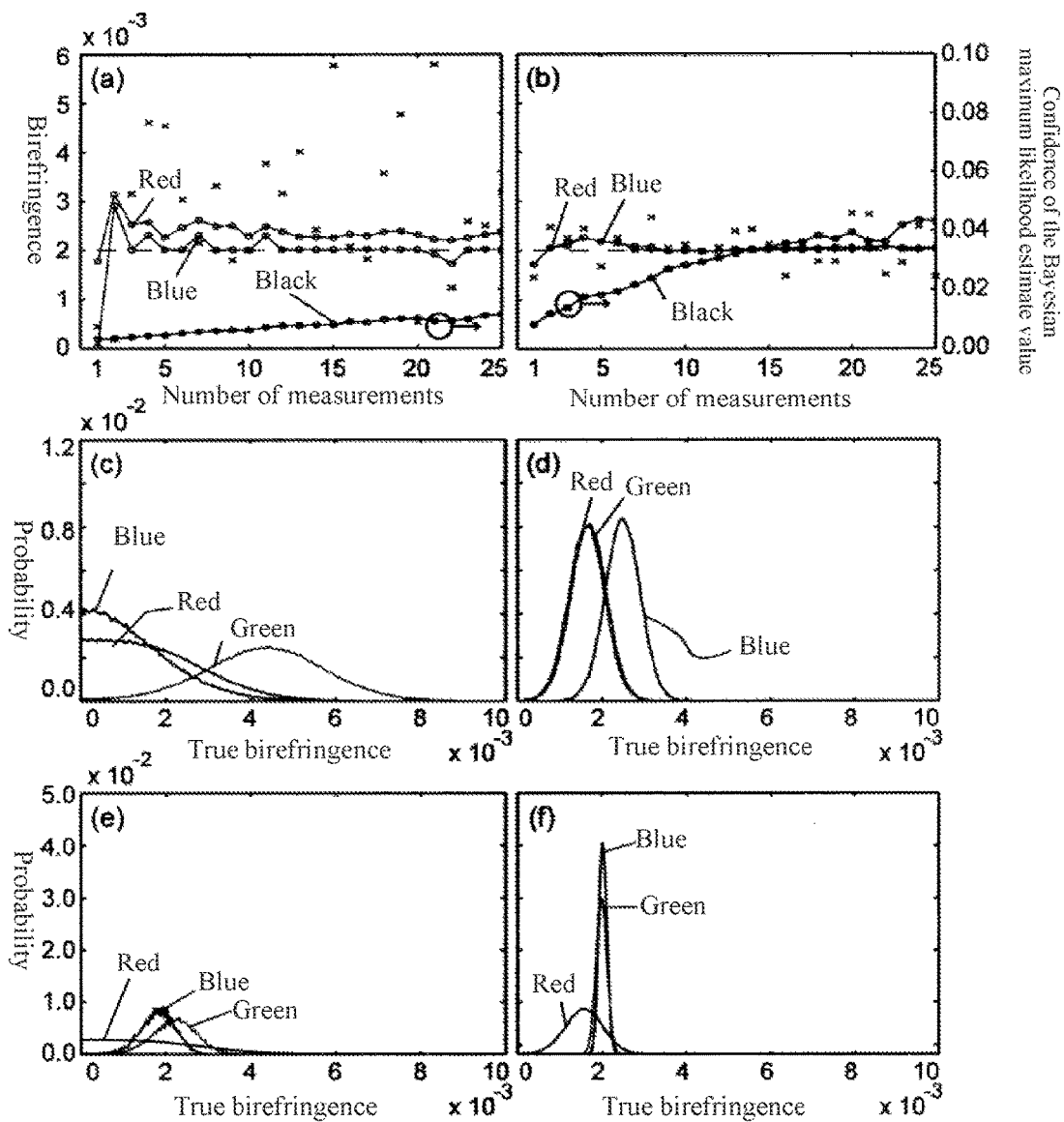

[FIG. 5]
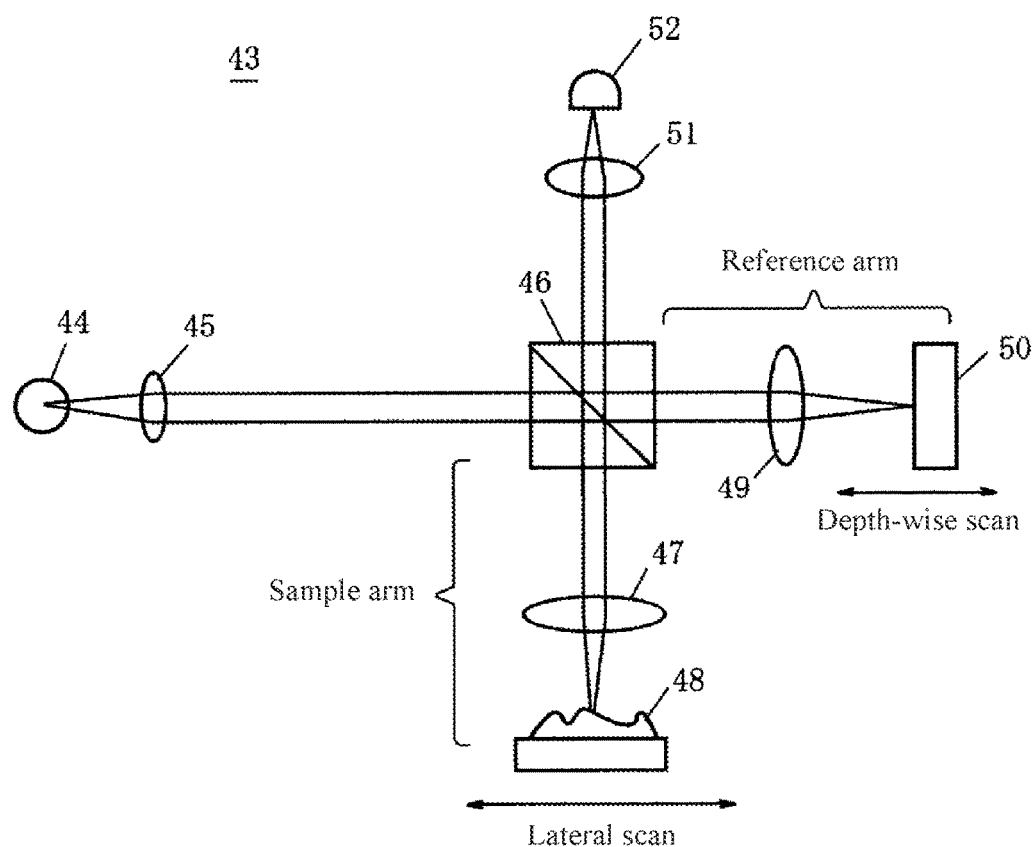

POLARIZATION-SENSITIVE OPTICAL IMAGE MEASURING SYSTEM AND PROGRAM INSTALLED IN SAID SYSTEM

This application is the U.S. National Phase under 35 U.S.C. §371 of International Application PCT/JP2015/066002, filed Jun. 3, 2015, which claims priority to Japanese Patent Application No. 2014-118159, filed Dec. 6, 2014. The International Application was published under PCT Article 21(2) in a language other than English.

TECHNICAL FIELD

The present invention relates to the technical field of optical coherence tomography (OCT), and more specifically to a polarization-sensitive optical image measuring system equipped with a polarization-sensitive optical image measuring unit (also referred to as "polarization-sensitive optical coherence tomograph" (PS-OCT)) capable of extracting local birefringence (polarization) information.

In other words, the present invention relates to a polarization-sensitive optical image measuring system that uses polarized light as incident light to understand the birefringence-based polarization dependence of a sample (measuring target) as the sample's polarization information to allow for accurate quantitative measurement of more detailed structures of the sample.

Also, the present invention relates to a polarization-sensitive optical image measuring system characterized by accurate quantitative measurement of histological birefringence based on Bayes statistics, as well as a program installed in such system.

BACKGROUND ART

Conventionally, OCT has been used to understand the internal information, or specifically the differential structure represented by backward scattering, reflectance distribution, and refractive index distribution, of the target (sample), in a non-destructive manner at high resolution.

"Optical coherence tomography" (OCT) is a non-destructive tomography technique used in the field of medicine, etc. (refer to Patent Literature 1). One advantage of OCT is that, because it uses light as a measurement probe, OCT can be used to measure the reflectance distribution, refractive index distribution, spectral information, and polarization information (birefringence distribution), etc., of the measuring target (sample).

The basic OCT 43 is built on the Michelson interferometer, whose principles are explained in FIG. 5. Light emitted from the light source 44 is parallelized by the collimator lens 45, and then split into reference light and object light by the beam splitter 46. The object light is collected onto the measuring target 48 by the object lens 47 in the object arm (sample arm), upon which it is scattered/reflected and then returns to the object lens 47 and beam splitter 46.

On the other hand, the reference light transmits through the object lens 49 in the reference arm, upon which it is reflected by the reference mirror 50 and returns to the beam splitter 46 through the object lens 49. The reference light, thus returning to the beam splitter 46, enters the collecting lens 51 together with the object light, and both lights are collected onto the photo-detector 52 (photo-diode, etc.).

For the OCT light source 44, a light source of low temporal coherence light (where it is extremely difficult for lights emitted from the light source at different times to interfere with each other) is used. With the Michelson interferometer using a light source of low temporal coherence light, an interference signal shows up only when the distance from the reference arm is roughly equivalent to the distance from the object arm. As a result, measuring the intensities of interference signals with the photo-detector 52 by changing the optical path difference ($\tau$) between the reference arm and object arm gives relationship between the interference signal and the optical path difference (interferogram).

The shape of this interferogram represents the reflectance distribution of the measuring target 48 in the depth direction, where one-dimensional scan in the axial direction reveals the structure of the measuring target 48 in the depth direction. As described above, the OCT 43 uses optical path length scan to measure the structure of the measuring target 48 in the depth direction.

Such axial-direction (A direction) scan can be combined with mechanical scan in the lateral direction (B direction) (B scan) to perform two-dimensional scan in order to obtain a two-dimensional cross-section image of the measuring target. For the scanner that performs this lateral-direction scan, one constituted in such a way that the measuring target is moved directly, or that the measuring target is fixed and the object lens is shifted, or that the measuring target and object lens are fixed and the angle of the galvano-mirror placed near the pupillary surface of the object lens is rotated, is used, among others.

Extensions of the basic OCT mentioned above include the swept source OCT (SS-OCT) that scans the wavelengths of the light source to obtain spectral interference signals, and the spectral domain OCT that uses a spectrometer to obtain spectral signals. The latter is divided into the Fourier domain OCT (FD-OCT, refer to Patent Literature 2) and the PS-OCT (refer to Patent Literature 3).

With the swept source OCT, the wavelength of the light source is changed with a high-speed wavelength scanning laser and the light source scan signals obtained simultaneously with the spectral signals are used to rearrange the interference signals, to which signal processing is applied, to obtain a three-dimensional optical tomography image. It should be noted that, with the swept scan OCT, a monochromator can be used as the means for changing the wavelength of the light source.

The Fourier domain OCT is characterized in that a spectrometer is used to obtain a wavelength spectrum of the reflected lights from the measuring target and then this spectral intensity distribution is Fourier-converted to take out signals in the real space (OCT signal space), and with this Fourier domain OCT, the cross-section structure of the measuring target can be measured by scanning in the X-axis direction, without having to scan in the depth direction.

The PS-OCT is an optical coherence tomograph that can successively modulate the polarization state of the beam that has been linearly polarized concurrently with B scan, to understand the polarization information of the sample (measuring target) and thereby measure a more detailed structure, and the anisotropy of the refractive index, of the sample.

To be more specific, the PS-OCT uses a spectrometer to obtain a wavelength spectrum of the reflected lights from the measuring target, just like the Fourier domain OCT does, where the incident light and reference light are each passed through a ½ wave plate, ¼ wave plate, etc., to be polarized horizontally linearly, vertically linearly, linearly at 45 degrees, or circularly, while the reflected light from the measuring target and reference light are superimposed and passed through a ½ wave plate, ¼ wave plate, etc., after which the horizontal polarization components alone, for example, are entered into the spectrometer to cause interference, and the object light components in specific polarization states are taken out and Fourier-converted. This PS-OCT does not require depth-wise scan, either.

BACKGROUND ART LITERATURE

Patent Literature

Patent Literature 1: Japanese Patent Laid-open No. 2002-310897
Patent Literature 2: Japanese Patent Laid-open No. Hei 11-325849
Patent Literature 3 Japanese Patent Laid-open No. 2004-028970

SUMMARY OF THE INVENTION

Problems to be Solved by the Invention

The aforementioned polarization-sensitive optical image measuring unit has been successful as an "observation" technology that uses birefringence as a contrast source; however, a number of problems still remain in establishing the quantification performance of such unit.

Earnest research and development by the group comprised by the inventors of the present invention has revealed that the birefringence measurement using a polarization-sensitive optical image measuring unit is subject to a non-negligible bias in the low signal strength range. In the range where this bias exists, accurate quantitative measurement of birefringence is not possible using a polarization-sensitive optical image measuring unit.

The present invention aims to remove this birefringence measurement bias of a polarization-sensitive optical image measuring unit in the low signal strength range, and an object of the present invention is to achieve a polarization-sensitive optical image measuring system equipped with a polarization-sensitive optical image measuring unit capable of accurate quantitative measurement.

Means for Solving the Problems

To achieve the aforementioned object, the present invention provides a polarization-sensitive optical image measuring system equipped with a polarization-sensitive optical image measuring unit, as well as a computer installed with a program for processing image data (measured data) obtained by the polarization-sensitive optical image measuring unit, wherein such polarization-sensitive optical image measuring system is characterized in that the computer has an input device, an output device, a CPU, and a storage device, and functions, according to the program, as: a means for processing noise-containing OCT signals obtained by measuring the sample using a birefringence calculation algorithm, to obtain measured birefringence values representing birefringence values measured in the presence of noise; a means for statistically changing the noise using Monte Carlo calculations and then processing the result with the algorithm, and repeating this process to simulate a measured birefringence distribution to determine the noise characteristics of the measured birefringence values; a means for repeating the Monte Carlo calculations by assuming different values for the noise level and the true birefringence value, respectively, to form three-dimensional histogram information showing how frequently a combination of given true birefringence value, SN ratio, and measured birefringence value appears; a means for assuming specified measured birefringence values and SN ratios from the three-dimensional histogram information to take out a true birefringence probability density distribution; and a means for estimating true birefringence values from the true birefringence probability density distribution.

To achieve the aforementioned object, the present invention provides a program installed in a computer of a polarization-sensitive optical image measuring system equipped with a polarization-sensitive optical image measuring unit, as well as such computer that has an input device, an output device, a CPU, and a storage device, and which processes the image data obtained by the polarization-sensitive optical image measuring unit, wherein such program is characterized in that it causes the computer to function as: a means for processing noise-containing OCT signals obtained by measuring the sample using a birefringence calculation algorithm, to obtain measured birefringence values representing birefringence values measured in the presence of noise; a means for statistically changing the noise using Monte Carlo calculations and then processing the result with the algorithm, and repeating this process to simulate a measured birefringence distribution to determine the noise characteristics of the measured birefringence values; a means for repeating the Monte Carlo calculations by assuming different values for the noise level and the true birefringence value, respectively, to form three-dimensional histogram information showing how frequently a combination of given true birefringence value, SN ratio, and measured birefringence value appears; a means for assuming specified measured birefringence values and SN ratios from the three-dimensional histogram information to take out a true birefringence probability density distribution; and a means for estimating true birefringence values from the true birefringence probability density distribution.

Preferably the computer functions as a means for performing the measurement multiple times and obtaining the true birefringence probability density distribution for each measured value, and then multiplying all birefringence probability density distributions, to obtain the final true birefringence probability density distribution.

Preferably the true birefringence value is an expected value of true birefringence value obtained from the true birefringence probability density distribution.

Preferably the true birefringence value is the maximum likelihood value, or specifically the true birefringence value that maximizes the true birefringence probability density distribution.

Preferably the computer functions as a means for obtaining the confidence of the maximum likelihood value based on the true birefringence probability density distribution.

Preferably when the sample is measured multiple times, only one pixel point among the specified locations on the sample is scanned multiple times, in order to measure many birefringence values at such one pixel point on the sample.

Preferably when the sample is measured multiple times, multiple pixel points including one pixel point among the specified locations on the sample are scanned, in order to measure the birefringence value at each of such multiple pixel points among the specified locations on the sample.

Preferably when the sample is measured, multiple pixel points including one pixel point among the specified locations on the sample are scanned once, in order to measure multiple birefringence values at such multiple pixel points among the specified locations.

Preferably the computer functions as a means for displaying an image based on the true birefringence values in simulated colors, where, regarding this display in simulated colors, its brightness is determined by the strength of the OCT signal, its color is determined by the maximum likelihood value of birefringence, and its density is determined by the confidence of the maximum likelihood value.

Effects of the Invention

According to the present invention, the true birefringence can be estimated even when it exists on the peripheral border (near an equivalent phase delay of 0 πrad) of the theoretically determined birefringence measurement area, which has heretofore been impossible, and the birefringence measurement bias of the polarization-sensitive optical image measuring unit in the low signal strength range can be removed, and therefore accuracy higher than a conventional polarization OCT unit can be achieved.

A program pertaining to the present invention can be installed in virtually all polarization OCT units with minimal hardware modifications.

BRIEF DESCRIPTION OF THE DRAWINGS

FIG. 1 Drawing showing a general constitution of a PS-OCT system pertaining to the present invention.

FIG. 2 Drawing showing an image processing computer constituting the PS-OCT system pertaining to the present invention.

FIG. 3 Drawing showing the test result in a test example of the present invention.

FIG. 4 Drawing showing the test result in a test example of the present invention.

FIG. 5 Drawing explaining a conventional OCT.

MODE FOR CARRYING OUT THE INVENTION

A mode for carrying out a polarization-sensitive optical image measuring system and a program installed in such system, pertaining to the present invention, is explained below by referring to the drawings based on an example.

The polarization-sensitive optical image measuring system pertaining to the present invention is equipped with a polarization-sensitive optical image measuring unit, as well as an image processing unit for processing the image data (measured data) obtained by the polarization-sensitive optical image measuring unit.

The image processing unit uses a standard computer, and the program pertaining to the present invention is installed in the computer and causes it to function as a means for processing the image data obtained by the polarization-sensitive optical image measuring unit.

The following first explains the constitutions of the polarization-sensitive optical image measuring unit and image processing unit (computer) that constitute the foundation of the present invention, and then explains the characteristic constitutions of the present invention, such as a means by which the computer functions according to the program of the present invention which is installed in the computer.

(Polarization-Sensitive Optical Image Measuring Unit)

The polarization-sensitive optical image measuring unit is explained with the PS-OCT in mind, and although the PS-OCT itself is already known in Japanese Patent No. 4344829, etc., it is the underlying technology of the present invention and therefore its overview is explained.

The polarization-sensitive optical image measuring unit pertaining to the present invention uses an EO modulator (polarization modulator/electro-optical modulator) to successively modulate the polarized beam (beam that has been linearly polarized by a polarizer) from the light source simultaneously (synchronously) as B scan (scan performed in one direction on the plane vertical to the depth direction of the sample), and then splits this successively modulated polarized beam, and scans one split beam as the incident beam and irradiates it onto the sample to obtain the reflected light (object light), while using the other split beam as the reference light, to perform OCT measurement based on spectral interference of the two.

And, the constitution of the unit is characterized in that, of the spectral interference components, the vertical polarization component (V) and horizontal polarization component (H) are measured simultaneously using two photodetectors, to obtain Jones vectors expressing the polarization characteristics of the sample (H image and V image).

FIG. 1 is a drawing showing a general constitution of the optical system of a polarization-sensitive optical image measuring unit pertaining to the present invention. The polarization-sensitive optical image measuring unit 1 shown in FIG. 1 is equipped with optical elements such as a light source 2, polarizer 3, EO modulator 4, fiber coupler (optical coupler) 5, reference arm 6, sample arm 7, and spectrometer 8. The optical system of this polarization-sensitive optical image measuring unit 1 uses fibers 9 to interconnect the optical elements; however, the structure may be of a type where they are not connected with fibers (free-space type).

For the light source 2, a super luminescent diode (SLD) having a broadband spectrum is used. Or, the light source 2 can be a pulse laser. A collimator lens 11, a polarizer 3 that linearly polarizes the light from the light source 2, an EO modulator (polarization modulator/electro-optical modulator) 4 whose phase advance axis is set in the 45° direction, a collecting lens 13, and a fiber coupler 5, are connected to the light source 2, in this order.

The EO modulator 4 sinusoidally modulates the voltage applied to the EO modulator 4 by fixing the phase advance axis in the 45° direction, to successively change the phase difference (retardation) between the phase advance axis and the phase delay axis orthogonal to it, so that when the light emitted from the light source 2 and (vertically and) linearly polarized by the polarizer 3 enters the EO modulator 4, it is modulated from linearly polarized light to elliptically polarized light, to linearly polarized light, and so on, according to the aforementioned modulation periods. For the EO modulator 4, any commercially available EO modulator can be used.

A reference arm 6 and a sample arm 7 are connected to the fiber coupler 5 via a branching fiber 9. A polarization controller 10, a collimator lens 11, a polarizer 12, a collecting lens 13, and a reference mirror (fixed mirror) 14, are provided on the reference arm 6, in this order. The polarizer 12 of the reference arm 6 is used to select an appropriate direction so that the intensity of the light returning from the reference arm 6 does not change even when the polarization state is modulated as described above. This direction (linear polarization direction) adjustment by the polarizer 12 is performed together with the polarization controller 10.

A polarization controller 15, a collimator lens 11, a fixed mirror 24, a galvano-mirror 16, and a collecting lens 13, are provided on the sample arm 7, in this order, and the incident beam from the fiber coupler 5 is scanned by the two-axis galvano-mirror 16 and irradiated onto the sample 17. The reflected light from the sample 17 returns to the fiber coupler 5 as the object light, is superimposed with the reference light, and the superimposed light is sent to a spectrometer 8 as an interference beam.

The spectrometer 8 is equipped with a polarization controller 18, a collimator lens 11, a diffraction grating (polarization-sensitive volume phase holographic type) 19, a Fourier conversion lens 20, a polarization beam splitter 21, and two photo-detectors 22, 23, which are connected in this order. In this embodiment, line CCD cameras (one-dimensional CCD cameras) are used for the photo-detectors 22, 23. The interference beam sent from the fiber coupler 5 is collimated by the collimator lens 11 and split by the diffraction grating 19 into an interference spectrum.

The interference spectral beam split by the diffraction grating 19 is Fourier-converted by the Fourier conversion lens 20 and split into horizontal and vertical components by the polarization beam splitter 21, after which the components are detected by the two line CCD cameras (photo-detectors) 22, 23, respectively. These two line CCD cameras 22, 23 are used to detect the phase information of both the horizontal and vertical polarization signals, which means that the two line CCD cameras 22, 23 must contribute to the formation of one and the same spectrometer.

It should be noted that the polarization controllers 10, 15, 18 provided at the reference arm 6, sample arm 7, and spectrometer 8, respectively, adjust the initial polarization state of the respective beams sent from the light source 2 to the reference arm 6, sample arm 7, and spectrometer 8, and control the polarization state after successive modulation at the EO modulator 4 to maintain a relationship of constant amplitude and constant relative polarization state between the reference light and object light, and also maintain a constant amplitude and a constant relative polarization state between them at the spectrometer 8 connected to the fiber coupler 5.

Additionally, the EO modulator 4 is stopped when the spectrometer 8, including the two line CCD cameras 22, 23, is calibrated. The reference light is blocked, and a glass slide and a reflective mirror are placed on the sample arm 7. This layout assures that the horizontal and vertical polarization components will have the same peak positions. And, OCT signals from the rear face of the glass slide and the reflective mirror are detected by the spectrometer 8 including the two line CCD cameras. The phase difference between the OCT signal peaks is monitored.

This phase difference must have zero depth in all optical axis directions. Next, the signals are windowed and reverse-Fourier-converted to obtain a complex spectrum at the spectrometer 8 including the two line CCD cameras 22, 23. Since this phase difference should be zero at all frequencies, phase difference values are monitored to align the physical positions of the two line CCD cameras 22, 23 so that the phase difference becomes the smallest.

Light from the light source 2 is linearly polarized, and this linearly polarized beam is passed through the EO modulator 4 to successively modulate its polarization state. In other words, the EO modulator 4 sinusoidally modulates the voltage applied to the EO modulator 4 by fixing the phase advance axis in the 45° direction, to successively change the phase difference (polarization angle/retardation) between the phase advance axis and the phase delay axis orthogonal to it, so that when the light emitted from the light source 2 and (vertically and) linearly polarized by the linear polarizer enters the EO modulator 4, it is modulated from linearly polarized light to elliptically polarized light, to linearly polarized light, and so on, according to the aforementioned modulation periods.

Then, B scan is performed simultaneously with the successive modulation of the polarization state of the linearly polarized beam by the EO modulator 4. To be specific, the EO modulator 4 performs modulation successively for multiple periods during a single B scan. Here, one period corresponds to a time period during which the polarization angle (retardation) φ changes from 0 to 2 π. In other words, the polarization of light from the polarizer is modulated successively from linear polarization (vertical polarization) to elliptical polarization, to linear polarization (horizontal polarization), and so on, during this one period.

As the polarization of polarized beam is successively modulated this way, the sample arm 7 performs B scan by scanning the incident beam over the sample 17 via the galvano-mirror 16 and, at the spectrometer 8, the horizontal polarization component and vertical polarization component of the interference spectrum of the object light, which is the reflected light of the incident beam, and the reference light, are detected by the two line CCD cameras 22, 23. This way, two A-B scan images corresponding to the horizontal polarization component and vertical polarization component, respectively, are obtained from a single B scan.

As described above, the polarization of polarized beam is modulated successively for multiple periods during a single B scan, where the polarization information of the horizontal polarization component and that of the vertical polarization component, detected, respectively, by the two line CCD cameras 22, 23 during each period (one period) of successive modulation constitutes the polarization information for one pixel. During one period of successive modulation, polarization information is detected by the two line CCD cameras 22, 23 in synchronization with the detection timing signals, by determining the number of detections (retrievals) such as four times, eight times or other number as deemed appropriate.

The data of two A-B scan images thus obtained from a single B scan is put through one-dimensional Fourier conversion in the direction of B scan. Then, the 0th, 1st and −1st peaks appear. Now, the 0th peaks are extracted and this data alone is used to perform reverse Fourier conversion, to obtain H0 and V0 images. Similarly, the 1st peaks are extracted and this data alone is used to perform reverse Fourier conversion, to obtain H1 and V1 images.

From the H0 and H1 images, Jones matrix components J (1,1) and J (1,2), among the components J (1,1), J (1,2), J (2,1) and (2,2) expressing the polarization characteristics of the sample 17, can be obtained. Also from the V0 and V1 images, Jones matrix components J (2,1) and J (2,2), among the components J (1,1), J (1,2), J (2,1) and (2,2) expressing the polarization characteristics of the sample 17, can be obtained.

This way, information containing four polarization characteristics is obtained from a single B scan. Then, when these four sets of information are each Fourier-converted in the direction of A scan just like under the standard FD-OCT, four A-B images of data (measured data) corresponding to the respective polarization characteristics, where the 1st peak has the depth-direction information of the sample 17, can be obtained.

The image data obtained by the polarization-sensitive optical image measuring unit 1 of the aforementioned constitution is input to a computer 30 used as an image processing unit. This computer 30 is a standard computer and has an input part 31, an output part 32, a CPU 33, a storage device 34, and a data bus 35, as shown in FIG. 2.

The image data processing program installed in the polarization-sensitive optical image measuring system, both pertaining to the present invention, is a program stored in the storage unit 34 of the computer 30, and this program causes the computer 30 to function as a means for removing the bias of birefringence measurement in the low signal strength range to allow for accurate quantitative measurement of birefringence with the polarization-sensitive optical image measuring system based on the PS-OCT image data input to the input part 31.

The foregoing is one example of polarization-sensitive optical image measuring system; however, the scope of use of the present invention is not limited to this example, and the present invention can be applied to all polarization-sensitive optical image measuring systems capable of measuring the polarization phase difference and the birefringence obtained by multiplying the polarization phase difference by a constant, as well as the scattering intensity distribution and the signal-to-noise ratio obtained by dividing the scattering intensity distribution by the system noise level, of a sample.

(Characteristic Constitutions of the Present Invention)

The characteristic constitutions of the polarization-sensitive optical image measuring system and the program (image data processing program) installed in such system, both pertaining to the present invention, or specifically a means by which the computer functions and how the computer operates according to the program, etc., are explained below.

Overview:

First, an overview is provided below. The polarization-sensitive optical image measuring unit (referred to as "polarization OCT") represents an observation technology based on measuring the birefringence and using the measured birefringence as a contrast source; however, birefringence measurement is subject to a non-negligible bias and deviation in birefringence especially in a surrounding range of low SN ratios (signal-to-noise ratios) and low signal strengths, which makes accurate quantitative measurement impossible.

The present invention removes this deviation in birefringence and makes accurate quantitative measurement possible. The present invention is characterized in that, to the foregoing end, it uses the OCT data processing technology of expressing the relationship between the measured birefringence and true birefringence by the Bayes' law (or Bayes' theorem), and then using this relationship and the Bayes estimation means to estimate the true birefringence value (Bayesian maximum likelihood estimate value, as described later) not affected by the bias, from the measured birefringence.

To constitute this Bayes estimation means, the function called "likelihood function" (under the present invention, this function expresses the equipment characteristics of the polarization OCT) is required. Traditionally, the equipment characteristics of the polarization OCT are associated with high, complex non-linearity that prevents calculation of this likelihood function.

Accordingly, the polarization-sensitive optical image measuring system and the program installed in such system, both pertaining to the present invention, are characterized in that they constitute the OCT data processing technology whereby the numerical calculation means called "Monte Carlo method" is used to numerically obtain this likelihood function based on the image data from the polarization OCT, and the aforementioned Bayes estimation means is used to estimate the true birefringence accordingly. It should be noted that the value obtained by multiplying the birefringence by a constant represents the value of polarization phase delay; that is, the present invention is also characterized in that the true value of polarization phase delay is obtained.

In addition, the present invention is characterized by a means for removing the system error among measured values (or specifically, measurement bias) from the true value by using the values from multiple polarization OCT measurements. This means is realized by statistically processing the distribution of birefringence values measured under the condition of the presence of noise (also referred to as "measured birefringence values" in this Specification and under the present invention).

Overall Flow and Means:

Among the means as which the computer of the polarization-sensitive optical image measuring system pertaining to the present invention function according to the installed program pertaining to the present invention, the chief means are explained first according to an overall flow of the applicable operations.

(1) The OCT data processing technology under the present invention has means for obtaining the distribution characteristics of measured birefringence using the Monte Carlo method. The specific means function (operate) in the following order, respectively, according to the program installed in the computer of the polarization-sensitive optical image measuring system.

(1)-1

First, according to the program installed in the computer of the polarization-sensitive optical image measuring system under the present invention, the computer functions as a means for modeling noise as complex Gaussian noise to be added to the complex OCT signal (raw signal measured for the purpose of calculating the birefringence), and then adding this noise to a randomly set noise-free complex OCT signal to model a noise-containing OCT signal, and processing this noise-containing OCT signal with the algorithm (non-linear algorithm) used by the polarization OCT to obtain the birefringence from the OCT signal, to obtain the birefringence value measured in the presence of noise (measured birefringence value).

(1)-2

Next, the computer functions as a means for statistically changing the noise (randomly so that the noise simulates Gaussian noise) according to Monte Carlo calculations, performing the process in (1)-1, and repeating this to simulate a measured birefringence distribution and thereby determine the (non-linear) noise characteristics of measured birefringence values.

(1)-3

Next, the computer functions as a means for repeating these Monte Carlo calculations by assuming various noise levels (=SN ratios) and various true birefringence values, to obtain three-dimensional histogram information that represents how frequently a combination of given true birefringence value, SN ratio, and measured birefringence value appears. This three-dimensional histogram is expressed by the three-dimensional function $f(b,\beta,\gamma)$ described later.

Here, by assuming a given measured birefringence value and an effective SN ratio (assign a given measured birefringence value b1 and an effective SN ratio 1), a one-dimensional histogram of true birefringence can be retrieved from this three-dimensional histogram. In this Specification, this is expressed as "indexing a three-dimensional histogram by the measured birefringence value and SN ratio."

The histogram of true birefringence thus retrieved represents a probability density distribution of values that may be taken by the true birefringence, which is unknown, when the aforementioned measured birefringence value and SN ratio are assumed to have been measured in a given measurement.

(2) The computer functions as a means for estimating the ultimately true birefringence value according to (2)-1 or (2)-2 below.

(2)-1

The true birefringence value is estimated by obtaining an expected value of true birefringence value from the true birefringence probability density distribution obtained above. (Expected value)

(2)-2

As for the true birefringence value, the maximum likelihood value of true birefringence can be estimated by selecting the maximum likelihood value for true birefringence probability density distribution (or specifically, the true birefringence value that maximizes the true birefringence probability density distribution).

(3) If multiple measurements were performed, the computer performs the processing in (1) on each measurement to obtain a true birefringence probability density distribution for each measured value. The computer functions as a means for obtaining the ultimately true birefringence probability density distribution (=combined true birefringence probability density distribution) by multiplying all of the true birefringence probability density distributions thus obtained.

(4) The computer functions, if multiple measurements have been performed, as a means for estimating the true birefringence value according to (4)-1 or (4)-2 below.

(4)-1

The true birefringence value is estimated by obtaining an expected value of true birefringence value from the combined true birefringence probability density distribution above. (Expected value)

(4)-2

The maximum likelihood value of true birefringence can be estimated by selecting the maximum likelihood value for combined true birefringence probability density distribution (or specifically, the true birefringence value that maximizes the combined true birefringence probability density distribution).

With respect to (1) to (4) above, all of the means in (1) and the means specified in (2)-2 and (4)-2 are referred to as "Bayesian maximum likelihood estimation means (Bayesian maximum likelihood estimator)" in this Specification.

Details of Each Means:

The following explains, along the above overall operation flow, the details of each means as which the computer of the polarization-sensitive optical image measuring system pertaining to the present invention functions according to the installed program pertaining to the present invention.

As a premise of these explanations, the polarization OCT-measured birefringence distribution is determined by three parameters, including the effective SN ratio (denoted by $\gamma$ in this Specification), true birefringence value (denoted by $\beta$ in this Specification), and inter-vector angle (denoted by $\zeta$ in this Specification).

The inter-vector angle $\zeta$ refers to the angle between the two vectors on the Poincaré sphere that represent the two types of incident polarized lights used in the polarization OCT measurement. It should be noted that the inter-vector angle $\zeta$ is a value determined by the polarization OCT system, and it is a fixed value. Considering this, the polarization OCT-measured birefringence distribution is determined by the effective SN ratio $\gamma$ and true birefringence value $\beta$.

The effective SN ratio $\gamma$ is a quantity defined as the harmonic average of all SN ratios, each obtained as a SN ratio corresponding to a different incident polarized light with respect to each of the multiple OCT signals used in the calculation of birefringence (or specifically, all SN ratios, each obtained with respect to the incident polarized light for each OCT signal). It should be noted that the measured birefringence value is denoted by b in this Specification.

Under the Monte Carlo method used in (1) of the overall flow above, a measured birefringence distribution is simulated by statistically changing noise, to determine the non-linear noise characteristics of measured birefringence values ((1)-2). Furthermore, similar Monte Carlo calculations are combined with the various settings of true birefringence value $\beta$ and SN ratio $\gamma$, to build a three-dimensional histogram expressed by the three-dimensional function $f(b,\beta,\gamma)$ ((1)-3).

After that, the measured birefringence value, which is the result obtained by Monte Carlo calculations, is fixed (assumed), or specifically the histogram is indexed by the measured birefringence value b, to obtain the true birefringence probability density distribution which was originally based on set parameters (expressed by the one-dimensional function $f(\beta;b,\gamma)$).

Such means is mathematically equivalent to "applying Bayes' law to the measured birefringence distribution obtained under a given true birefringence value and an effective SN ratio, to obtain the true birefringence value in the condition where a given measured birefringence value and an effective SN ratio were measured."

In other words, it is not that Bayes' law is applied to (1); instead, Bayes' law is the very theoretical rationale if the processing in (1) is considered to give the true birefringence probability density distribution, as intended by the inventors of the present invention.

The three-dimensional histogram is expressed by the three-dimensional function $f(b,\beta,\gamma)$, as mentioned above. $f(b;\beta,\gamma)$ represents a probability density distribution relative to b at a specific true birefringence $\beta$ and a specific effective SN ratio $\gamma$. Accordingly, integrating $f(b;\beta,\gamma)$ relative to b results in "1" regardless of the values of $\beta$ and $\gamma$. Also, this distribution is characterized only by the two parameters of $\beta$ and $\gamma$.

Here, assuming a given measured birefringence value b1 and a SN ratio $\gamma$1 means assigning constants b1 and $\gamma$1 to b and $\gamma$.

Once constants are assigned, as above, b and $\gamma$ are no longer variables and the function f becomes one-dimensional function $f(\beta)$. This condition is denoted by one-dimensional function $f(\beta;b1,\gamma1)$. b and $\gamma$ with a subscript are constants, while those without a subscript are variables. This is what "index a three-dimensional histogram to take out a one-dimensional histogram" means.

A histogram of measured birefringence values obtained by measuring one point on the measuring target multiple times, is virtually similar in shape to $f(b;\beta,\gamma)$. Accordingly, in reality a histogram of measured birefringence values can be substituted for $f(b;\beta,\gamma)$ after standardizing it to achieve an integral solution of "1" relative to b.

The true birefringence probability density distribution is a probability density distribution of true birefringence $\beta$ in the condition where a specific measured birefringence value b and an effective SN ratio $\gamma$ were measured, and is denoted by $p(\beta;b,\gamma)$. By using Bayes' law, the true birefringence $\beta$ probability density distribution $p(\beta;b,\gamma)$ can be obtained from the measured birefringence probability density distribution $f(b;\beta,\gamma)$ according to Equation 1.

$$p(\beta;b,\gamma) \propto f(b;\beta,\gamma)\pi(\beta) \qquad \text{[Equation 1]}$$

$\pi(\beta)$ is a beforehand-predicted true birefringence probability density distribution whose significance is described later. In Equation 1, β and γ in f (b;β,γ) are treated as values, or parameters, which determine the shape of f (b;β,γ) when it is considered as a function of b.

f (β;b1,γ1), shown below in Equation 2, is a function obtained by assigning (b1,γ1) to f (β;b,γ) as measured values of (b,γ). When this Equation 2 is referenced, f (b;β,γ) is rewritten as f (β;b,γ). This rewritten f is a function of β, and b and γ are parameters that determine the shape of this function.

$$p_1(\beta) \equiv p(\beta;b,\gamma)|_{(b,\gamma)=(b_1,\gamma_1)} \propto f(\beta;b_1,\gamma_1) \quad \text{[Equation 2]}$$

However, these differences are merely based on how the equations are interpreted (understood), and f (b;β,γ) and f (β;b,γ) are mathematically exactly identical. Put more generally, f is a three-dimensional function (β;b,γ) comprised of b, β and γ. f (β;b,γ) is called "likelihood function."

In Equation 2, "|(b,γ)=(b1,γ1)" means that "as a result of measurement, (b1,γ1) is obtained as a measured value of (b,γ); accordingly, in the equation on the left side of the vertical line, b1 is assigned to b and γ1 is assigned to γ."

So long as the true birefringence probability density distribution is obtained, it can be used to estimate the true birefringence value β. For example, the average estimate value (expected value) of true birefringence value β, in the condition where the effective SN ratio γ and measured birefringence value b were obtained by measurement, is obtained according to Equation 3 below. It should be noted that, in Equation 3, the average estimate value (expected value) of birefringence value β is denoted by the symbol β with the minus sign as a superscript.

$$\bar{\beta} = \int_{-\infty}^{+\infty} \beta p(\beta;b,\gamma) d\beta \quad \text{[Equation 3]}$$

Also, the maximum likelihood estimate value (most likely estimate) of true birefringence β is obtained by applying (assigning) f (β;b,γ) as obtained according to Equation 2, to Equation 4 below. It should be noted that the maximum likelihood estimate value of true birefringence β is denoted by the symbol β with "^" as a superscript. Also, "arg max" (argument of the maximum) means an original set in a domain where the function value is maximized. The symbol below "arg max" indicates the original part to be changed in order to maximize the function. In other words, the right term of Equation 4 gives the value of true birefringence β that maximizes the function.

$$\hat{\beta} = \underset{\beta}{\arg\max}\, p(\beta;b,\gamma) \quad \text{[Equation 4]}$$

It should be noted that the result of applying Equation 2 to Equation 4 is summarized in Equation 5 below. As mentioned earlier, π(β) is a beforehand-predicted true birefringence probability density distribution, the details of which are described later.

$$\hat{\beta}|_{(b,\gamma)=(b_1,\gamma_1)} = \underset{\beta}{\arg\max}\, f(\beta;b_1\gamma_1) \quad \text{[Equation 5]}$$

When the foregoing is organized, under the present invention the first step is to estimate a true birefringence probability density distribution in the condition where a given measured birefringence value, and an effective measured SN ratio corresponding thereto, are measured. For this estimation, the measured birefringence probability density distribution f (b;β,γ) calculated (determined) numerically according to the Monte Carlo method beforehand, and Equation 1, are used. Then, from the true birefringence probability density distribution obtained therefrom, the maximum likelihood value is obtained.

Incidentally, under the present invention an estimate value of true birefringence can be obtained from a single birefringence measurement (or specifically, from a single set of measured birefringence value and corresponding effective SN ratio). However, the estimation accuracy can be improved by performing multiple measurements.

First, the means for estimating the true birefringence through a single birefringence measurement is explained below. Then, as an extension of this, the means for estimating the true birefringence by utilizing the measured values obtained through multiple birefringence measurements is explained.

Assume that a measured birefringence value b1, and an effective SN ratio γ1, were obtained through a single measurement (the measured birefringence value and effective SN ratio are simultaneously acquired as a pair). Here, when Equation 1 is utilized, the true birefringence probability density distribution is expressed according to Equation 2.

In Equation 1, π(β) represents a beforehand-predicted true birefringence probability density distribution. This is considered preliminary knowledge on true birefringence. In general, no preliminary knowledge on true birefringence is available before the first measurement is performed. For this reason, π(β) is assumed to have a uniform distribution when the first measurement is used to estimate the true birefringence. In other words, η(β) is assumed as a constant.

When estimating the true birefringence from multiple birefringence measurements, the nth measurement uses the p (β;b,γ) obtained from the n−1th and earlier measurements, as π(β).

For example, assume that birefringence and effective SN ratio were measured twice and that (b1,γ1) and (b2,γ2) were obtained. From the values measured first (b1,γ1), the true birefringence β probability density distribution p1 (β;b1,γ1) is obtained according to Equation 2.

Next, the measured values obtained by the second measurement (b2,γ2) are assigned to Equation 1, to obtain the true birefringence probability density after the second measurement. Here, the p1 (β;b1,γ1) obtained earlier is used as π(β).

Now, the true birefringence β probability density distribution after the second measurement is expressed by Equation 6 below.

$$p_2(\beta) \equiv p(\beta;b,\gamma)|_{(b,\gamma)=(b_1,\gamma_1),(b_2,\gamma_2)} \propto f(\beta;b_2,\gamma_2) f(\beta;b_1,\gamma_1) \quad \text{[Equation 6]}$$

It is clear that, by repeating the above, the true birefringence β probability density distribution from the nth measurement is expressed by Equation 7 below. In Equation 7, Π indicates the product of all results of the function f (β;bi,γi) where i changes from i=1 to i=N. If i=1 and N=3, for example, H is calculated by f (β;b1,γ1)×f (β;b2,γ3)×f (β;b3,γ3).

$$p_N(\beta) \equiv p(\beta;b,\gamma)\bigg|_{(b,\gamma)=(b_1,\gamma_1),\ldots(b_N,\gamma_N)} \propto \prod_{j=1}^{N} f(\beta;b_1,\gamma_1) \quad \text{[Equation 7]}$$

This way, the maximum likelihood value of birefringence based on multiple measurements can be derived by expanding a method similar to the estimation process based on a single measurement. The maximum likelihood value of true birefringence from the nth measurement is obtained by assigning the $P_\mathcal{N}(\beta)$ expressed by Equation 7 to the p ($\beta$;b,$\gamma$) in Equation 4, and is expressed by Equation 8.

$$\hat{\beta}\Big|_{(b_1,\gamma_1),\ldots (b_N,\gamma_N)} \equiv \underset{\beta}{\mathrm{argmax}} \prod_{i=1}^{N} f(\beta; b_1, \gamma_1) \quad \text{[Equation 8]}$$

One benefit of the Bayesian means for maximum likelihood estimation is that it gives not only an estimate value (Bayesian maximum likelihood estimate value) of true birefringence, but also a true birefringence probability density distribution. This probability density distribution can be used to obtain the confidence of the estimate value of true birefringence.

Equation 9 represents an equation for obtaining the confidence of a given maximum likelihood estimate value of true birefringence (denoted by $\beta$ with "^" as a superscript) by using this true birefringence probability density distribution. Here, the aforementioned confidence is represented by the left term of Equation 9. $\Delta\beta$ indicates the width of the preset confidence interval of true birefringence, and the center of this confidence interval gives the maximum likelihood estimate value of true birefringence.

$$\mathcal{L}(\hat{\beta};\Delta\beta) = \int_{\hat{\beta}-\Delta\beta/2}^{\hat{\beta}+\Delta\beta/2} p_\mathcal{N}(\beta) d\beta; b_1, \gamma_1) \quad \text{[Equation 9]}$$

Here, $P_\mathcal{N}(\beta)$ is a probability density function that has been standardized to give an integral solution of "1" for the interval S relative to $\beta$. S represents the true birefringence range. This confidence is used to convert the birefringence distribution tomography of the measured sample to an image in simulated colors.

It should be noted that, to estimate the Bayesian maximum likelihood value based on Equation 8, the likelihood function f ($\beta$;b,$\gamma$) must be obtained beforehand. The likelihood function is obtained from the true birefringence probability density distribution, by using the measured birefringence distribution f (b;$\beta$,$\gamma$) that has been calculated (determined) numerically beforehand according to the Monte Carlo method based on the OCT noise model, and by also using Equation 1, to obtain the true birefringence probability density distribution. Furthermore, the maximum likelihood value can be obtained from the likelihood function.

The Monte Carlo calculations under the present invention, performed in (1) of the overall flow above, are explained below using a specific example.

A single set of Monte Carlo calculations consists of 65,536 repetitions of a simulated measurement (numerically simulated measurement, hereinafter referred to as "simulated measurement"). In each simulated measurement, two Jones matrixes are generated first. What this means is that Jones matrixes at two points on the sample, which are required in one birefringence measurement, are generated by a single simulated measurement. These Jones matrixes are determined in such a way that the birefringence determined by the difference between the polarization phase differences of the two has a given true value $\beta$.

In the aforementioned OCT noise model, complex Gaussian noise is added to the respective elements in the Jones matrixes. The standard deviation of noise is set in such a way that the desired effective SN ratio $\gamma$ at which to perform simulation under this Monte Carlo method is realized. In each simulated measurement above, the measured birefringence value b is obtained using calculations equivalent to those performed by the polarization-sensitive imaging unit used in the embodiment of the present invention.

A distribution of the measured birefringence values b in the condition where a specific true birefringence $\beta$ and an effective SN ratio $\gamma$ are assumed, can be obtained by a single set of Monte Carlo calculations as described above. Here, a shifted averaged histogram is obtained from the (obtained 65,536) values of b. It should be noted that this shifted averaged histogram itself is a one-dimensional histogram, and when two or more such one-dimensional histograms are obtained by changing the two parameters $\beta$ and $\gamma$, a three-dimensional histogram is formed.

The histogram has 1,024 bins, and the size of each bin is set according to the Freedman-Diaconis method. This shifted averaged histogram is used as the maximum likelihood function f ($\beta$;b,$\gamma$) after multiplying a constant so that the total sum of all counts in the histogram becomes "1" (or specifically, after standardizing it). It should be noted that, while an arbitrary bin size must be "set" in order to create a histogram, the Freedman-Diaconis method is a calculation formula generally used to uniquely determine a bin size.

The Monte Carlo calculations performed in (1)-3 in the overall flow above are repeated with respect to 201 true birefringence values of 0.000044 in resolution in a range of 0 to 0.0088, as well as effective SN ratios of 1 dB in resolution in a range of 0 to 40 dB.

The area of obtained true birefringence values can be obtained by assigning, to the equation "polarization phase delay/(2 kZd)," the depth-direction distance (Zd) at the simulation measurement point where the above two Jones matrixes are assumed to be measured, as well as the area of 0 to $\pi$ radians where the polarization phase delay can be measured. Here, k represents the wave number of the probe light of the polarization-sensitive imaging unit used in the embodiment. This gives 0 to $\pi$/2 kZd as the area of obtained true birefringence. In this example, Zd is 37 μm (6 pixels).

In (1)-3 in the overall flow above, Monte Carlo calculations are repeated by changing the values of $\beta$ and $\gamma$ as mentioned above. This way, the maximum likelihood function f ($\beta$;b,$\gamma$) is obtained as a three-dimensional numerical function.

Additionally, the resolution of this maximum likelihood function can be improved by the Lanczos interpolation method. In this example, the resolution is improved so that 1,024 true birefringence values can be obtained. Here, the resolution of birefringence estimation becomes 0.0000086.

Once the Monte Carlo calculations are performed, the three-dimensional histogram obtained as a result is saved in the storage device in the form of three-dimensional array data. In the true birefringence estimation process, the saved three-dimensional data are read and indexed using the measured values (bi,$\gamma$i).

Here, the dimensions of the three-dimensional array are b, $\gamma$ and $\beta$, so indexing it by bi, $\gamma$i gives a probability density distribution of $\beta$ relative to bi, $\gamma$i, or specifically, a likelihood function. This likelihood function f ($\beta$;bi,$\gamma$i) is a one-dimensional array and obtained for each measurement.

If multiple measurements were performed, a distribution pi (Equation 7) is obtained posteriorly after each of the measurements. Then, the posterior distribution obtained after the last measurement, and Equation 8, are used to obtain the maximum likelihood estimate value.

It should be noted that the maximum likelihood estimation means under the present invention requires that each point on the sample be measured multiple times. For the measurement protocol (scanning pattern, method) used here, two different protocols are available.

Protocol 1 represents a method of performing B scan repeatedly at one point (one pixel) on the sample, involving multiple scans of the same point on the sample. As a result, many birefringence values are measured at the same point on the sample.

Protocol 2 represents a method of performing B scan once at one point on the sample. Here, only one measured value is obtained for one point on the sample; however, multiple points (multiple pixels) in a small range called "kernel" near this point are used to obtain an estimate value.

Under this protocol 2, an estimate value of maximum likelihood value is obtained by using the birefringence values obtained at multiple measured pixels that are slightly away from each other, which means that this is an approximative means. This protocol 2 is based on the premise that the true birefringence does not differ significantly inside the kernel.

Notwithstanding this premise, this protocol 2 is effective when performing B scan multiple times at one point on the sample is difficult, such as when a living body or other moving sample, etc., is measured to estimate a birefringence value.

By displaying the birefringence values as obtained above as an image in simulated colors, the observer can observe the birefringence characteristics of the structure more easily. On this image in simulated colors, the brightness of each pixel is determined by the scattering intensity, or specifically the OCT signal strength, while its color (hue) is determined by the estimate value of birefringence. Also, the density (color saturation) is determined by the confidence of the estimate value.

In other words, the structure of the sample is shown by brightness, while its birefringence is shown by the color of each pixel. Also, pixels whose estimate value of birefringence is of extremely high confidence are colored, while pixels whose estimate value of birefringence is of high confidence are shown in black and white.

Here, the scattering intensity is defined by the average intensity of the two OCT images close to the reference depth position of the OCT, among the four OCT images obtained by the two photo-detectors (refer to the two line CCD cameras 22, 23 in FIG. 1) constituting the JMOCT (polarization OCT capable of obtaining the Jones matrix components representing the polarization characteristics of the sample as mentioned above). This image is generally referred to as "scattering intensity image not dependent on birefringence."

Test Example

The inventors of the present invention verified the performance of the maximum likelihood estimation means (device) under the present invention, using numerical simulation based on the Monte Carlo method. The test example pertaining to this performance verification is explained below. This verification was conducted in two ways, as described below.

First, in the first verification, simulation was performed based on the Monte Carlo method by assuming seven true birefringence values $\beta$ and then assuming 36 effective SN ratios $\gamma$ for each birefringence value in 1-dB steps from 5 dB to 40 dB.

Here, the depth-direction distance Zd at the two measurement points used in the calculation of birefringence was assumed as 37 μm. For all combinations of the effective SN ratios $\gamma$ and true birefringence $\beta$, 1,024 measurements were simulated according to the Monte Carlo method and the resulting numerically simulated measured values were used to obtain Bayesian maximum likelihood estimate values and average estimate values (expected values) of birefringence.

The Bayesian maximum likelihood estimate values and average estimate values of birefringence thus obtained were converted to polarization phase difference values for easy interpretation, respectively, and shown in FIG. 3. In FIG. 3, the horizontal axis represents the effective SN ratio (ESNR) [dB], while the vertical axis represents the polarization phase difference value (phase retardation) [dB]. "Blue" indicates the blue lines, while "Red" indicates the red lines.

In FIG. 3, the blue lines and red lines represent the Bayesian maximum likelihood estimate values and average estimate values, respectively, as the functions of effective SN ratios. The true birefringence values (set values of simulation) corresponding to the respective lines are denoted by horizontal dotted lines.

The results show that, when the effective SN ratio is 6 dB or more, an appropriate estimate value is obtained by the Bayesian maximum likelihood estimation means. On the other hand, the average estimate value deviates significantly from the true value even at relatively high effective SN ratios of 15 to 20 dB. This deviation of average estimate value is particularly prominent when the true value is 0 radian or $\pi$ radian.

It is clear from these results that the Bayesian maximum likelihood estimation means gives a more appropriate estimate value than the average estimation means does, especially when the effective SN ratio is low.

In the second verification, effective SN ratios of 10 dB and 20 dB were assumed to simulate 25 measurements according to the Monte Carlo method. The true birefringence value $\beta$ was assumed as 0.002, and the depth-direction distance Zd at the measurement point was assumed as 37 μm.

FIG. 4 (*a*) and FIG. 4 (*b*) show the results at 10 dB and 20 dB, respectively. In these figures, simulated measured values are denoted by "x." True birefringence values (set values of simulation) are denoted by horizontal dotted lines.

In FIGS. 4 (*a*), (*b*), "Blue" indicates the blue line, "Red" indicates the red line, and the horizontal axis represents the number of measurements used in the estimation. Also, the vertical axis represents the birefringence value and the confidence relative to the Bayesian maximum likelihood estimate value, where the Bayesian maximum likelihood estimate value is denoted by the blue line with circles, while the average estimate values are denoted by a red line. In FIGS. 4 (*a*), (*b*), each circle denotes an accurate estimate value. Also, the black line with circles indicates the confidence corresponding to the obtained Bayesian maximum likelihood estimate value (quantity defined in paragraphs 0119 and 0120).

As is evident from FIGS. 4 (*a*), (*b*), the Bayesian maximum likelihood estimate value indicated by the blue line becomes asymptotically closer to the true value as the number of measured values used increases, at both 10 dB and 20 dB. The confidence also increases at the same time. On the other hand, it is evident from FIG. 4 (*a*) that, at 10 dB, the average estimate value indicated by the red line asymptotically converges to a value deviating from the true value, or specifically a biased value, even when the number of measured values used increases.

The likelihood functions f ($\beta$;b,$\gamma$) corresponding to the 1st, 11th and 21st simulated measurements are shown in FIG. 4 (*c*) and FIG. 4 (*e*). Here, FIG. 4 (*c*) shows the measurements simulated at 10 dB, while FIG. 4 (*e*) shows the measurements simulated at 20 dB. Also, the horizontal axis represents the true birefringence value, while the vertical axis represents the probability density.

Here, in FIGS. 4 (c), (e), "Red," "Green" and "Blue" indicate the red, green, and blue lines, respectively, and the red, green, and blue lines represent the 1st, $11^{th}$, and 21st likelihood functions, respectively. Also, the horizontal axis represents the true birefringence value, while the vertical axis represents the probability density.

Similarly, in FIGS. 4 (d), (f), "Red," "Green" and "Blue" indicate the red, green and blue lines, respectively, and the horizontal axis represents the true birefringence value, while the vertical axis represents the probability density.

FIG. 4 (d) (at 10 dB) and FIG. 4 (f) (at 20 dB) each show the true birefringence probability density distributions (posterior distributions) (p1($\beta$),p11($\beta$),p21($\beta$)) obtained by using the 1st measurement (red line), 11th measurement (green line), and 21st measurement (blue line).

Clearly, the posterior distribution becomes sharper as the number of measurements used increases. This sharpening of the posterior distribution with an increase in the number of measurements corresponds to the increasing likelihood (or specifically, confidence of estimation) as shown in FIG. 4 (a) (at 10 dB) and FIG. 4 (b) (at 20 dB).

Incidentally, at 10 dB, the maximum likelihood estimate value becomes closer to the true value, even when the sharpness of the posterior distribution is relatively low. This deserves attention.

The aforementioned verification (simulation) was repeated 50 times to verify the estimate value for the quantity of bias (deviation from the true value) and also for repeatability.

At 10 dB, the average and standard deviation of the estimate values obtained by 50 repetitions were 0.00197±0.00039 (average±standard deviation) for the maximum likelihood estimate value, and 0.00235±0.00029 for the average estimate value. (As mentioned above, the true birefringence value is set to 0.00200.)

At 20 dB, the average and standard deviation of the estimate values obtained by 50 repetitions were 0.00200±0.00009 for the maximum likelihood estimate value, and 0.00201±0.00009 for the average estimate value. Based on these results, the Bayesian maximum likelihood estimation means clearly has a smaller measurement bias (=deviation from the true value) than the average estimation method (method currently used in general).

The foregoing explained, based on an example, a mode for implementing the polarization-sensitive optical image measuring system and the program installed in the computer of such system, both pertaining to the present invention; however, the present invention is not limited to such example, and it goes without saying that various examples may apply to the extent permitted by the technical items described in the scope of patent claims.

INDUSTRIAL FIELD OF APPLICATION

The present invention is a technology that can be applied widely to polarization OCT units, and that is also expected to boost the performance of polarization OCT in all fields where application of polarization OCT is expected. In particular, the present invention can be utilized as a polarization OCT unit in the field of medical technology, as described below.
(1) Diagnosis of risks of glaucoma and myopia based on birefringence measurement of the sclera.
(2) Observation of progress and maintenance of treatment effects after glaucoma surgery (trabeculectomy).
(3) Determination of risks presented by arterial sclerosis in the coronary artery.

DESCRIPTION OF THE SYMBOLS

1 PS-OCT (polarization-sensitive optical coherent tomograph: polarization-sensitive optical image measuring unit)
2 Light source
3, 12 Polarizer
4 EO modulator (polarization modulator/electro-optical modulator)
5 Fiber coupler (optical coupler)
6 Reference arm
7 Sample arm
8 Spectrometer
9 Fiber
10, 15, 18 Polarization controller
11 Collimator lens
13 Collecting lens
14 Reference mirror (fixed mirror)
16 Galvano-mirror
17 Sample
19 Diffraction grating
20 Fourier conversion lens
21 Polarization beam splitter
22, 23 Photo-detector (line CCD camera)
24 Fixed mirror
30 Computer (image processing unit)
31 Input part
32 Output part
33 CPU
34 Storage device
35 Data bus
43 OCT
44 Light source
45 Collimator lens
46 Beam splitter
47 Object lens inside the object arm (sample arm)
48 Measuring object (sample)
49 Object lens inside the reference arm
50 Reference mirror
51 Collecting lens
52 Photo-detector

What is claimed is:
1. A polarization-sensitive optical image measuring system equipped with a polarization-sensitive optical image measuring unit, as well as a computer installed with a program for processing an image data obtained by the polarization-sensitive optical image measuring unit, the polarization-sensitive optical image measuring system characterized in that the computer has an input device, an output device, a CPU, and a storage device, and functions, according to the program, as:

a means for processing noise-containing OCT signals obtained by measuring a sample using a birefringence calculation algorithm, to obtain measured birefringence values representing birefringence values measured in a presence of noise;

a means for statistically adjusting the noise using Monte Carlo calculations and then processing said noise with the algorithm, and repeating this process to simulate a measured birefringence distribution to determine noise characteristics of measured birefringence values;

a means for repeating the Monte Carlo calculations by assuming different values for noise level and true birefringence value, respectively, to form three-dimensional histogram information showing how frequently a combination of given true birefringence value, SN ratio, and measured birefringence value appears;

a means for assuming specified measured birefringence values and SN ratios from the three-dimensional histogram information to take out a true birefringence probability density distribution; and a means for estimating true birefringence values from the true birefringence probability density distribution.

2. A polarization-sensitive optical image measuring system according to claim 1, characterized in that the computer functions as a means for performing the measurement multiple times and obtaining the true birefringence probability density distribution for each measured value, and then multiplying all birefringence probability density distributions, to obtain a final true birefringence probability density distribution.

3. A polarization-sensitive optical image measuring system according to claim 1, characterized in that the true birefringence value is an expected value of true birefringence value obtained from the true birefringence probability density distribution.

4. A polarization-sensitive optical image measuring system according to claim 1, characterized in that the true birefringence value is a maximum likelihood value, or specifically the true birefringence value that maximizes the true birefringence probability density distribution.

5. A polarization-sensitive optical image measuring system according to claim 4, characterized in that the computer functions as a means for obtaining a confidence of the maximum likelihood value based on the true birefringence probability density distribution.

6. A polarization-sensitive optical image measuring system according to claim 2, characterized in that, when the sample is measured multiple times, only one pixel point among specified locations on the sample is scanned multiple times, whereby measuring many birefringence values at such one pixel point on the sample.

7. A polarization-sensitive optical image measuring system according to claim 2, characterized in that, when the sample is measured multiple times, multiple pixel points including one pixel point among specified locations on the sample are scanned, thereby measuring the birefringence value at each of such multiple pixel points among the specified locations on the sample.

8. A polarization-sensitive optical image measuring system according to claim 2, characterized in that, when the sample is measured, multiple pixel points including one pixel point among specified locations on the sample are scanned once, thereby measuring multiple birefringence values at such multiple pixel points among the specified locations.

9. A polarization-sensitive optical image measuring system according to claim 5, characterized in that the computer functions as a means for displaying an image based on the true birefringence values in simulated colors, where, regarding this display in simulated colors, its brightness is determined by a strength of the OCT signal, its color is determined by the maximum likelihood value of birefringence, and its density is determined by the confidence of the maximum likelihood value.

10. A computer readable no-transitory medium storing a program for a computer of a polarization-sensitive optical image measuring system equipped with a polarization-sensitive optical image measuring unit, as well as such computer that has an input device, an output device, a CPU, and a storage device, and that processes image data obtained by the polarization-sensitive optical image measuring unit, the program characterized in that it causes the computer to function as:

a means for processing noise-containing OCT signals obtained by measuring a sample using a birefringence calculation algorithm, to obtain measured birefringence values representing birefringence values measured in a presence of noise;

a means for statistically adjusting the noise using Monte Carlo calculations and then processing said noise with the algorithm, and repeating this process to simulate a measured birefringence distribution to determine noise characteristics of measured birefringence values;

a means for repeating the Monte Carlo calculations by assuming different values for noise level and true birefringence value, respectively, to form three-dimensional histogram information showing how frequently a combination of given true birefringence value, SN ratio, and measured birefringence value appears;

a means for assuming specified measured birefringence values and SN ratios from the three-dimensional histogram information to take out a true birefringence probability density distribution; and a means for estimating true birefringence values from the true birefringence probability density distribution.

11. A computer readable no-transitory medium storing a program according to claim 10, characterized in that it causes the computer to function as a means for performing the measurement multiple times and obtaining the true birefringence probability density distribution for each measured value, and then multiplying all birefringence probability density distributions, to obtain a final true birefringence probability density distribution.

12. A computer readable no-transitory medium storing a program according to claim 10, characterized in that the true birefringence value is an expected value of true birefringence value obtained from the true birefringence probability density distribution.

13. A computer readable no-transitory medium storing a program according to claim 10, characterized in that the true birefringence value is a maximum likelihood value, or specifically the true birefringence value that maximizes the true birefringence probability density distribution.

14. A computer readable no-transitory medium storing a program according to claim 13, characterized in that it causes the computer to function as a means for obtaining a confidence of the maximum likelihood value based on the true birefringence probability density distribution.

15. A computer readable no-transitory medium storing a program according to claim 11, characterized in that, when the sample is measured multiple times, only one pixel point among specified locations on the sample is scanned multiple times, thereby measuring many birefringence values at such one pixel point on the sample.

16. A computer readable no-transitory medium storing a program according to claim 11, characterized in that, when the sample is measured multiple times, multiple pixel points including one pixel point among specified locations on the sample are scanned, thereby measuring the birefringence value at each of such multiple pixel points among the specified locations on the sample.

17. A computer readable no-transitory medium storing a program according to claim 11, characterized in that, when the sample is measured, multiple pixel points including one pixel point among specified locations on the sample are scanned once, thereby measuring multiple birefringence values at such multiple pixel points among the specified locations.

18. A computer readable no-transitory medium storing a program according to claim 14, characterized in that the computer functions as a means for displaying an image based on the true birefringence values in simulated colors, where, regarding this display in simulated colors, its brightness is determined by a strength of the OCT signal, its color is determined by the maximum likelihood value of birefringence, and its density is determined by the confidence of the maximum likelihood value.

* * * * *